United States Patent
Gabbay

(10) Patent No.: US 6,685,625 B2
(45) Date of Patent: Feb. 3, 2004

(54) CURVED IMPLANTABLE SHEATH AND METHOD OF MAKING SAME

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 0 days.

(21) Appl. No.: 09/862,955

(22) Filed: May 22, 2001

(65) Prior Publication Data

US 2002/0036221 A1 Mar. 28, 2002

Related U.S. Application Data

(63) Continuation-in-part of application No. 09/669,821, filed on Sep. 26, 2000.

(51) Int. Cl.⁷ .................................................. A61F 2/04
(52) U.S. Cl. ..................... 600/36; 623/1.1; 623/23.72; 623/901
(58) Field of Search ................ 623/1.1, 1.3, 1.31, 623/1.13, 11.11, 12, 66.1, 916, 921, 925, 23.64–23.76, 901; 600/16, 36, 37; 606/151–158, 191, 194

(56) References Cited

U.S. PATENT DOCUMENTS

| | | | |
|---|---|---|---|
| 3,966,401 A | | 6/1976 | Hancock et al. |
| 4,502,159 A | * | 3/1985 | Woodroof et al. ............. 600/36 |
| 4,909,979 A | * | 3/1990 | Possis et al. .................. 264/230 |
| 4,990,131 A | * | 2/1991 | Dardik et al. .................. 600/36 |
| 6,334,872 B1 | * | 1/2002 | Termin et al. .............. 623/1.38 |
| 2002/0036220 A1 | * | 3/2002 | Gabbay ........................ 224/191 |

FOREIGN PATENT DOCUMENTS

WO    WO 00/33768 A1 * 6/2000 ............. A61F/2/06

OTHER PUBLICATIONS

Norwood, William I. Jr., MD, Phd. *Hypoplastic Left Heart Syndrome*. 1991; pp. 688–696.

"No–React", Product brochure of Shelhigh, Inc., Millburn, New Jersey, Copyright date unknown.

International Search Report for PCT/US0127159.

* cited by examiner

*Primary Examiner*—Urmi Chattopadhyay
(74) *Attorney, Agent, or Firm*—Tarolli, Sundheim, Covell & Tummino L.L.P.

(57) ABSTRACT

A method for making a curved implantable sheath includes placing a sheet of flexible material into engagement with a member having a curved surface having a desired configuration. The sheet and member are placed in a fixation solution so that the sheet assumes the configuration of the surface engaged thereby.

15 Claims, 6 Drawing Sheets

CURVED IMPLANTABLE SHEATH AND METHOD OF MAKING SAME

RELATED APPLICATION

This application is a continuation-in-part of U.S. patent application Ser. No. 09/669,821, which was filed on Sep. 26, 2000, and entitled SYSTEM AND METHOD FOR MAKING A CALOTTE-SHAPED IMPLANTABLE SHEATH.

TECHNICAL FIELD

The present invention relates to implantable tissue and, more particularly to a curved implantable sheath and to a method for making a curved sheath.

BACKGROUND

Various configurations of implantable structures are employed to help repair diseased and malformed organs and other tissue. By way of example, congenital cardiac malformations as well as other diseased conditions, require treatment, which can include drug therapy and/or surgery. Often times, it is necessary to replace or reconstruct an artery or other major vessel, such as the aorta or pulmonary artery.

In one particular condition, known as hypoplastic left heart syndrome, severe aortic valve hypoplasia and/or aortic valve atresia develop. As a result of such conditions, the aorta may be significantly underdevelop, providing a rudimentary ascending aorta having a diameter of about one to about four millimeters. Also as a consequence of limited outflow from the heart, the left ventricle develops abnormally and may be virtually absent.

Because certain curved shapes are difficult to reproduce, a generally flat sheath of biocompatible tissue typically is used for many types of procedures. In other cases a homograft, such as from a cadaver is used.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

One aspect of the present invention provides a method for making a curved implantable sheath. A sheet of flexible material is urged into engagement with a member having a curved surface of a desired configuration. The sheet and member are placed in a fixation solution so that the sheet assumes the configuration of the surface engaged thereby.

Another aspect of the present invention provides a method for making a sheath having a curved contour. The method includes mounting a sheet of a biological tissue material to an elongated member having a curved exterior portion. The sheet and elongated member are placed in a fixation solution so that at least part of the sheet is fixed to a configuration corresponding to the exterior portion of the elongated member. The sheet is separated from the elongated member to provide an elongated sheath of substantially biocompatible material having a desired curved contour.

According to another aspect of the present invention, the sheet can be formed to have a generally C-shaped cross section.

BRIEF DESCRIPTION OF THE DRAWINGS

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings, in which.

DESCRIPTION OF THE INVENTION

Various illustrative aspects of the present invention will now be described in connection with the following figures.

The present invention provides a system and method that may be used to fix tissue to a desired shape so as to better conform to contoured organs and tissue against which the tissue is to engage when implanted. While the following examples will be described with respect to forming a calotte-shaped sheath of tissue, those skilled in the art will understand and appreciate that other shapes, such as cylindrical sheaths and curved arches, also may be formed in accordance with the present invention.

Figure 1:
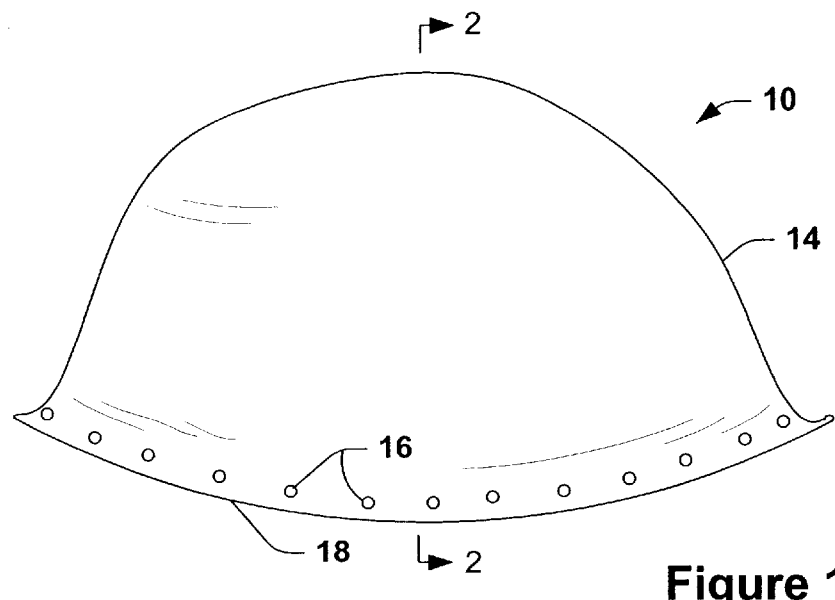
FIG. 1 is an example of a base member having a surface over which tissue may be fixed in accordance with the present invention.
Figure 2:
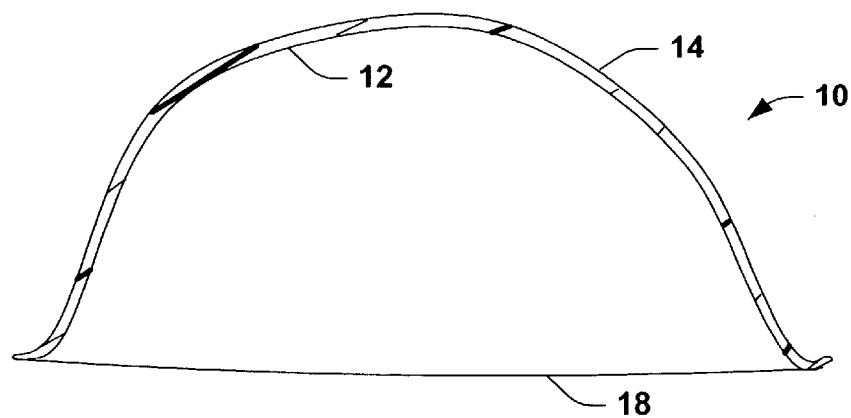
FIG. 2 is a cross-sectional view of the base member of FIG. 1 taken along line 2—2.

Turning now to FIGS. 1 and 2, a generally semi-spherical base 10 is illustrated. The base 10, which may be a bowl formed of a rigid material (e.g., a metal or plastic material), has an inner surface 12 and an outer surface 14. In this example, the inner surface 12 is curved in a convex manner and the outer surface 14 is curved in a generally concave manner.

In accordance with an aspect of the present invention, the inner and/or outer surfaces 12 and 14, respectively, may be dimensioned and configured to correspond to the shape of a selected part of a human brain. It is to be appreciated that other shapes and sizes may be utilized to process tissue to have a desired contour, such as for implantation in other types of surgical procedures. In addition, the inner surface 12 may be dimensioned to have radius of curvature that is less than the outer surface 14. The inner and outer surfaces 12 and 14 also may have different shapes or contours. As a result, differently dimensioned and/or shaped sheaths may be formed with the same base 10.

Figure 3:
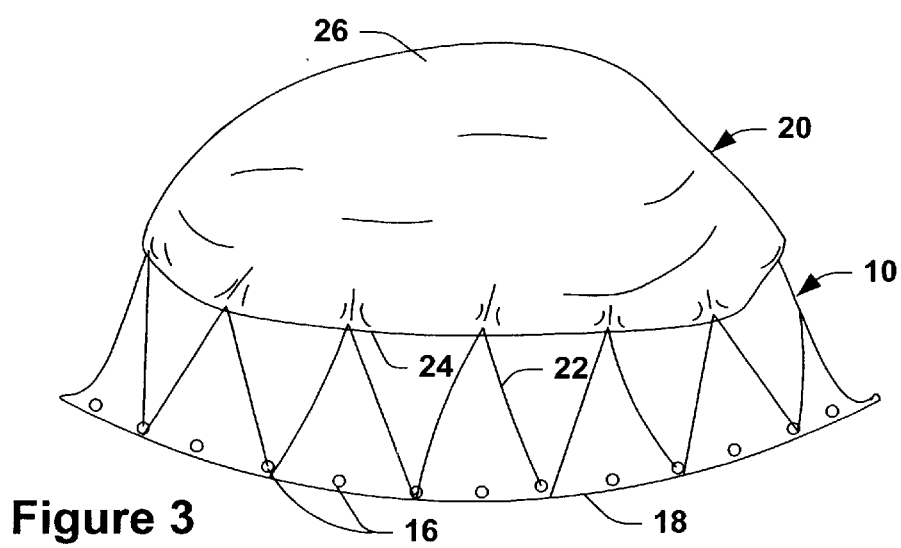
FIG. 3 is an example of tissue held against the surface of a base member in accordance with the present invention.

In this example, the base 10 also has a plurality of apertures 16 located near an open end 18 of the base. The apertures 16 provide a convenient way to secure a sheet of tissue 20 to the outer surface 14 of the base 10, such as shown in FIG. 3. The sheet of tissue 20 may be substantially any type of biological tissue. By way of example, the tissue may be animal pericardium (e.g., equine, bovine, porcine, etc.), collagen, animal dura mater, or other type of suitable sheet of tissue. To provide better results, the sheet of tissue should be a generally fresh, soft sheet of tissue. The sheet of tissue 20 may be in nearly any shape, such as rectangular, circular, elliptical, etc.

By way of illustration, one or more sutures 22 are sewn through a perimeter edge 24 of the tissue 20 so as to hold at least a substantial portion of the tissue in engagement with the outer surface 14 of the base 10. For the example when the tissue is animal pericardium, the smooth or visceral side of the pericardium should engage the outer surface 14 with the more rough side exposed. Typically at least a central part 26 of the tissue 20 is maintained completely against the surface 14, and it is this part of the tissue that is used to form a calotte-shaped sheath in accordance with an aspect of the present invention.

While the example of FIG. 3 illustrates sutures being utilized to temporarily attach the tissue relative to the base 10, it is to be appreciated that other means also may be utilized to hold the tissue relative to the base in accordance with an aspect of the present invention. For example, suitable hooks or clamps could be employed to secure the tissue relative to the base 10 or other appropriate structure.

Figure 4:
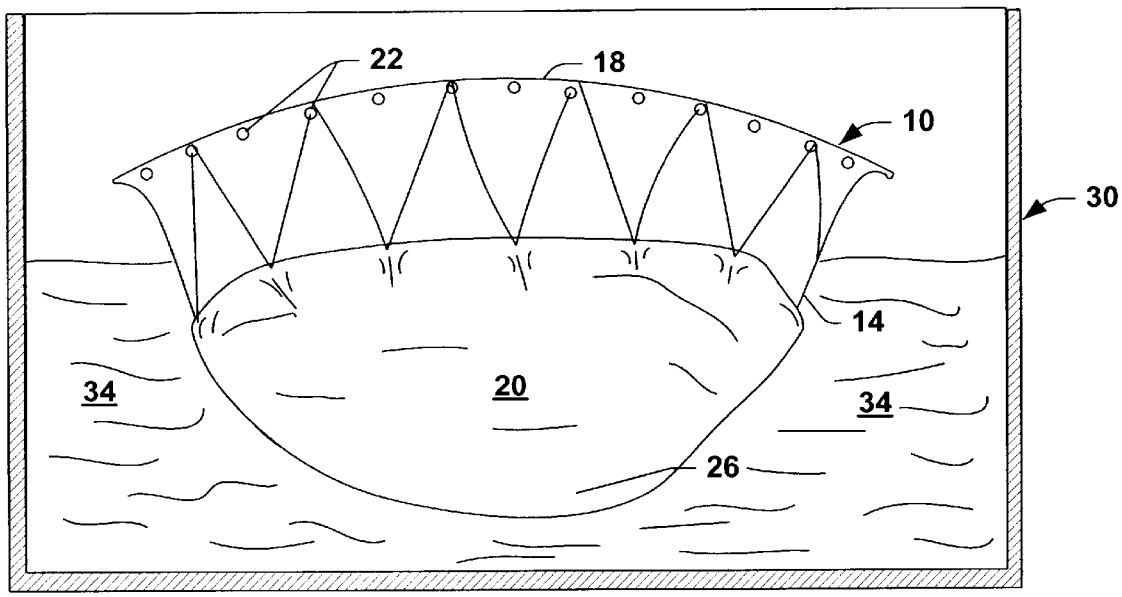
FIG. 4 is an example of tissue being fixed to a desired shape in accordance with the present invention.

FIG. 4. illustrates an example of a system 30 that may be employed to fix the tissue 20 to a desired shape in accordance with an aspect of the present invention. In this example, the system 30 includes a chamber 32 that contains a volume of a suitable fixation solution 34. The combination of the tissue 20 attached to the base 10 is immersed into the fixation solution 34 for sufficient period of time so as to fix the tissue that is exposed to the solution to substantially the same shape as the outer surface 14 of the base. By way of example, the fixation solution 34 is a solution that includes glutaraldehyde, which is well known in the art. A time period of about twenty-four hours in a glutaraldehyde solution should be sufficient to fix the tissue 20.

Figure 5:
FIG. 5 is an example of a calotte-shaped sheath produced from tissue treated in accordance with the present invention.

The tissue 20 may then be removed from the solution 34 and detached from the base 10. The tissue 20 is then trimmed to a desired size to form a calotte-shaped sheath 40, such as shown in FIG. 5. When the sheath 40 is to be used in neurosurgery as substitute dura mater, for example, the sheath may have diameter from about 10 cm to about 14 cm, although other sized sheaths also could be formed in accordance with an aspect of the present invention. The trimmed peripheral portion may be discarded or used to form other implantable tissue products.

After initial fixation and trimming, the calotte-shaped sheath 40 may be placed back in a suitable solution, such as may contain glutaraldehyde, for additional curing. In particular, the natural tissue sheath 40 further may be cross-linked with glutaraldehyde and undergo a detoxification process with heparin bonding, such as according to the NO-REACT® treatment process from Shelhigh, Inc. of Millburn, N.J. The NO-REACT® tissue treatment process helps improve the biocompatibility of the sheath 40.

Figure 6:
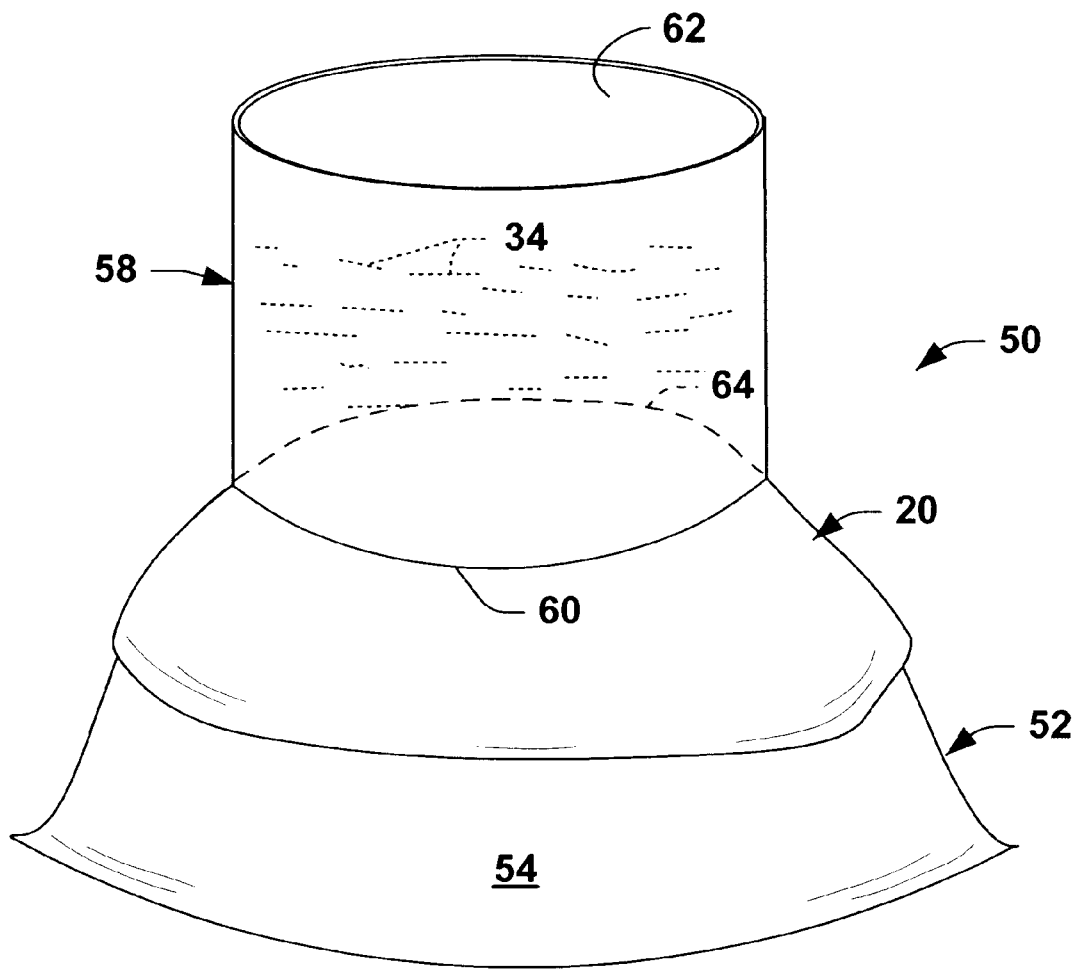
FIG. 6 is another example of tissue being fixed to a desired shape in accordance with the present invention.

FIG. 6 illustrates another system 50, in accordance with an aspect of the present invention, which may be employed to form an implantable calotte-shaped sheath 40. The system 50 includes a base 52 having a curved, generally semispherical (e.g. convex) outer surface 54. For example, the base 52 may be hollow bowl, although any structure having a desired outer surface 54 could be used. A sheet of biological tissue 20 is placed onto the outer surface 54 of the base 52, as shown in FIG. 6.

In contrast to the sutures and apertures utilized in the system of FIGS. 3 and 4, a generally tubular apparatus 58, such as a hollow cylinder, is used to hold the tissue 20 in a desired position relative to the base 52. In particular, the tubular apparatus 58 has a tissue-engaging end 60 that engages the tissue 20 and sandwiches the tissue between the outer surface 54 and the end 60. The engagement between the tissue-engaging end 60 and the tissue 20 may form a substantially liquid tight seal. In order to improve the seal, a rubber or other soft material may be provided at the end 60. As a result, an interior surface 62 of the tubular apparatus 58 and a portion 64 of the tissue 20 extending within the end 60 define a volume for holding a fixation solution 34. That is, the fixation solution 34 may be provided into the tubular apparatus 58 to fix the portion 64 of the tissue 20 within the annular end 60 to substantially the same shape as the outer surface contacted thereby. If some of the solution 34 leaks through the juncture between the tubular apparatus 58 and the tissue 20, the fluid simply would need to be replenished. Advantageously, the weight of the fixation solution 34 further helps to hold the central portion 64 of the tissue 20 against the outer surface 54 to promote a desired shape during fixation.

After fixing the tissue 20 for a suitable time period (e.g., about twenty-four hours), the tissue may then be removed from the system 50 and trimmed to form a calotte-shaped sheath 40, such as shown in FIG. 5.

While the apparatus 58 is shown and described as being generally cylindrical it is to be appreciated that other shapes also could be used in accordance with the present invention. Typically, however, the tissue-engaging end 60 of the apparatus should conform to the contour of the outer surface 54 and have a sufficient diameter so as to fix a desired portion 64 of the tissue 20.

Figure 7:
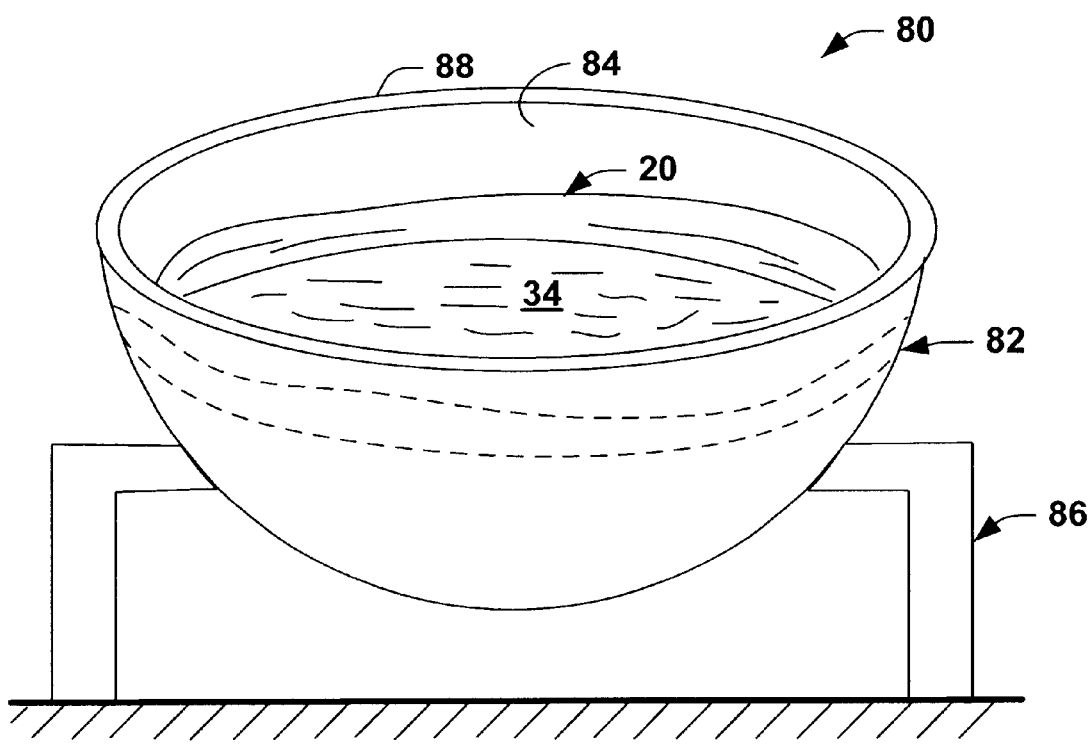
FIG. 7 is yet another example of tissue being fixed to a desired shape in accordance with the present invention.

FIG. 7 illustrates yet another example of a system 80 that may be utilized, in accordance with an aspect of the present invention, to form a calotte-shaped sheath 40 of tissue. The system 80 includes a base portion 82 having a convex inner surface 84. The base portion 82, for example, may be a bowl similar to the other system arrangements shown and described herein. An appropriate support apparatus 86 may be employed to hold the base portion 82 in a desired position, such that an open end 88 faces upwards. In this example, sheet of tissue 20 is placed against the inner surface 84 of the base. For the example where the tissue 20 is animal pericardium, the smooth side engages the inner surface 84. The tissue 20 may be smoothed out by hand (or by a suitable instrument) so that at least a substantial portion (e.g., a central portion) of the tissue 20 is substantially flush against the inner surface 84 the base 82.

After the tissue is at a desired position, a volume of a suitable fixation solution 34, such as may include glutaraldehyde, is added to a volume defined by the sheath 20 within the base 82. The weight of the fixation solution 34 helps maintain engagement between at least a substantial portion of the tissue 20 and the inner surface 84, thereby promoting fixation of the tissue to the desired shape. In order to facilitate engagement between the tissue 20 and the inner surface 84, a cup-shaped member, such as felt or other diffusable material, may be placed over the tissue within the base to help hold the tissue against the inner surface 84 of the base 82. After the tissue 20 has been fixed for a suitable time phase, the tissue may be removed and trimmed to a desired shape, such as to form the calotte-shaped sheath shown in FIG. 5.

FIGS. 8–12 and the accompanying description illustrate an example of a method that can be implemented to provide a curved sheath of tissue in accordance with an aspect of the present invention. For purposes of simplicity of illustration, identical reference numbers refer to corresponding parts throughout FIGS. 8–12.

Figure 8:
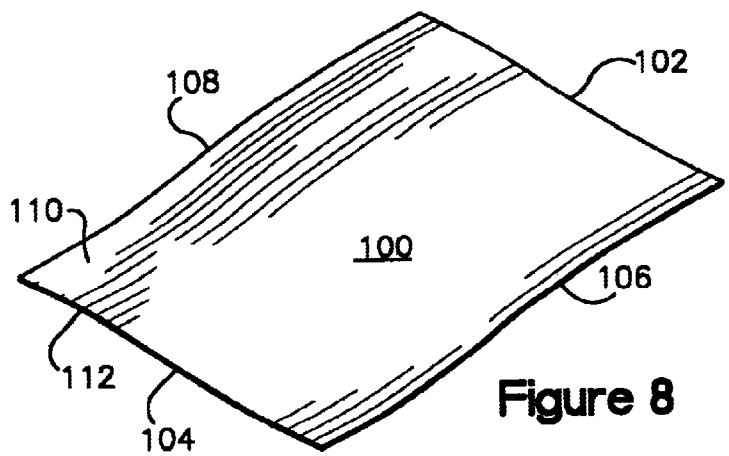
FIG. 8 is a generally flat sheet of flexible material.

FIG. 8 illustrates a generally flat sheet 100 of flexible material that can be utilized to form a curved sheath of tissue in accordance with an aspect of the present invention. The sheet 100 includes ends 102 and 104 that are spaced apart from each other by a pair of elongated side edges 106 and 108. For example, the sheet 100 can be a flexible sheet of animal tissue, such as pericardium or another suitable thin sheet of tissue (e.g., dura matter, molded collagen, etc.). When pericardium is used, the sheet 100 includes a visceral side 110 that is generally smoother than the other side 112.

Figure 9:
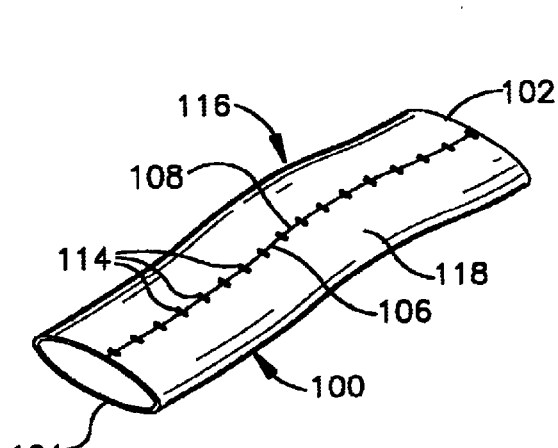
FIG. 9 is an example of a generally tubular structure that can be formed from the sheet of FIG. 8.

In accordance with an aspect of the present invention, the side edges 106 and 108 are urged toward each other so that the intermediate portion of the sheet 100 extending between such edges has a curved shape. As shown in FIG. 9, for example, the side edges 106 and 108 are connected together, such as by sutures 114, to form a tube 116 of the biological tissue material having a generally cylindrical sidewall 118. Other types of retaining mechanisms also could be utilized to secure the edges 106 and 108 relative to each other, such as clips, fasteners, etc.

Thus, from FIG. 9, it will be appreciated that the sheet 100 can be employed to form a generally cylindrical sidewall having desired diameters at each of its ends 102 and 104, which diameters can be the same or different. That is, the resulting structure 116 can be frusto-conical. Because, at this stage, the tissue of the sheet 100 is flexible (e.g., formed of relatively fresh natural tissue), it is flacid and thus tends to collapse to a relatively flat tube 116, such as shown in FIG. 9.

In accordance with an aspect of the present invention, part of the sheet 100 is urged against a curved surface. The combination of sheet 100 and curved surface are immersed in a fixation solution so that at least that part of the sheet 100 takes on the contour of the curved surface.

Figure 10:
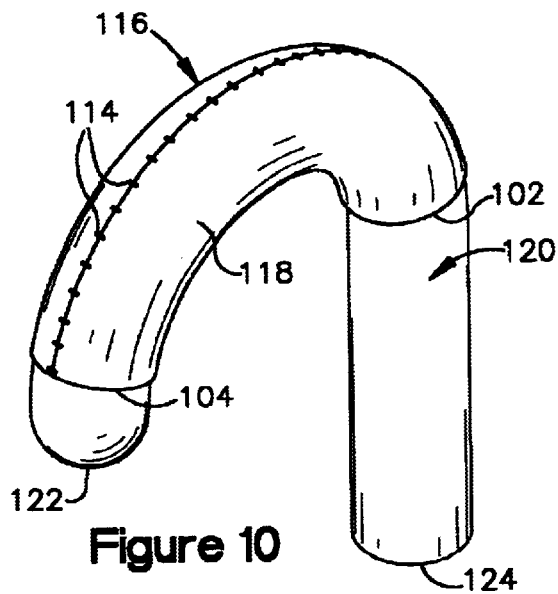
FIG. 10 is the tubular structure of FIG. 9 mounted over a curved member in accordance with the present invention.

With reference to the example of FIG. 10, the biological tube 116 is depicted as being mounted over a curved mandrel 120. As shown in FIG. 10, for example, the tube is mounted over a curved mandrel having a generally circular cross section. Alternatively, the mandrel 120 can have a varying cross-sectional diameter and/or have a plurality of ribs or circumferentially extending corrugations. The particular dimensions and configuration of the mandrel 120 can vary according to the desired shape and size of the tissue being formed in accordance with an aspect of the present invention.

In one aspect the elongated mandrel 120 extends arcuately between its ends 122 and 124. For example, the arcuate extent of the mandrel 120 has a radius of curvature that is greater than about forty-five degrees and, in another aspect, could have a radius of curvature greater than about ninety degrees, as shown in FIG. 10. The curved mandrel 120 also has an outer cross-sectional diameter that approximates or is slightly greater than the inner diameter of the biological tube 116. As a result, the tube 116 is held on the mandrel 120 by friction.

While FIGS. 9 and 10 have been shown and described as creating the tube 116 and then sliding the tube over the mandrel 120, it is to be understood that the sheet 100 could be wrapped around and secured relative to the mandrel. For example, the ends 106 and 108 of the sheet 100 can be urged around and secured relative to the mandrel, such as by sutures 114 or by clamps, retaining bands, and the like.

Figure 11:
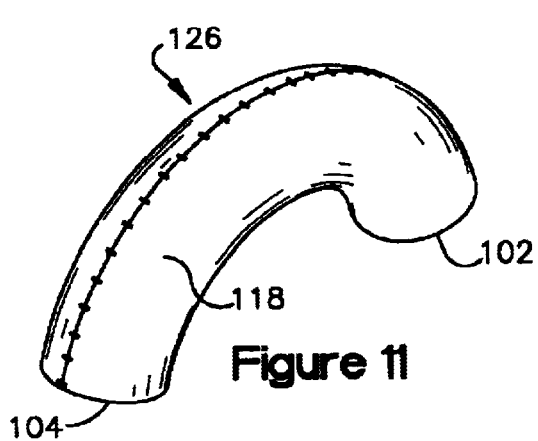
FIG. 11 is an example of a curved tubular sheath that can be produced in accordance with an aspect of the present invention.

In accordance with an aspect of the present invention, the assembly that includes the biological tube 116 and the curved mandrel 120 are immersed in a fixation solution, such as including an aldehyde solution (e.g., glutaraldehyde). Accordingly, at least the part of the sheet 100 exposed to the fixation solution assumes the contour of the mandrel 120 that such tissue engages. After appropriate fixation, the tube 116 can be removed from the mandrel 120 to provide a curved tubular sheath 126 such as shown in FIG. 11. Additional fixation may be implemented relative to the curved tubular sheath 126. As a result, the tubular sheath 126 is permanently fixed to provide an arcuately extending cylindrical sidewall 118 corresponding to the configuration of the mandrel 120.

Figure 12:
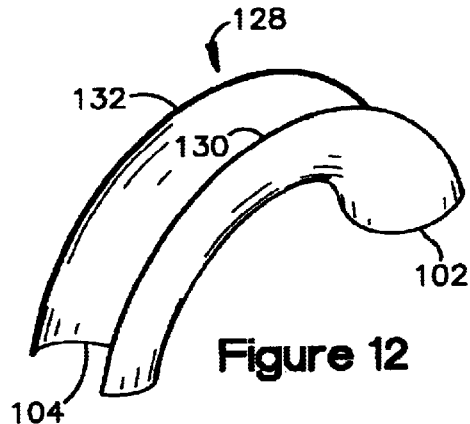
FIG. 12 is an example of a curved sheath of tissue in accordance with an aspect of the present invention.

In accordance with an aspect of the present invention, the tubular sheath 122 can be trimmed to a desired shape and size. In one particular aspect, as shown in FIG. 12, the suture line 114 and some adjacent tissue extending coextensively with the sheath 126 between the ends 102 and 104 can be excised from the tubular sidewall 118. As a result, an elongated curved sheath 128 of tissue is formed, which sheath has a generally C-shaped cross section extending between its ends 102 and 104. The sheath 128 has elongated side edges 130 and 132 that extend arcuately between the spaced apart ends 102 and 104 of the sheath. As a result, the sheath 128 has the appearance of a curved trough or gutter. Because of the fixation process, the sheath 128 maintains its C-shaped cross section (e.g., based on the circumference of the mandrel) as well as its arcuate length (e.g., corresponding to the radius of curvature of the mandrel).

The fixed tissue sheath 128 as well as the tubular sheath 126 can be detoxified to improve the biocompatibility thereof. By way of illustration, the sheath can be cross-linked with glutaraldehyde and undergo a detoxification process with heparin bonding, such as according to the NO-REACT® treatment process. The NO-REACT® tissue treatment process helps improve the biocompatibility of the sheath and render the sheath substantially cytocompatible.

The curved C-shaped cross section of the sheath 128 facilitates reconstruction and repair of vessels, such as part of a vessel enlargement. For example, the side edges 132 and 130 can be anastomosed to exposed side edges of a patient's vessel, such as an artery or vein. It is to be appreciated that the curved length of tubular material, such as shown in FIG. 11, also provides a useful conduit, such as may be employed to repair or replace a curved vessel or be attached to a heart valve prosthesis.

Figure 13:
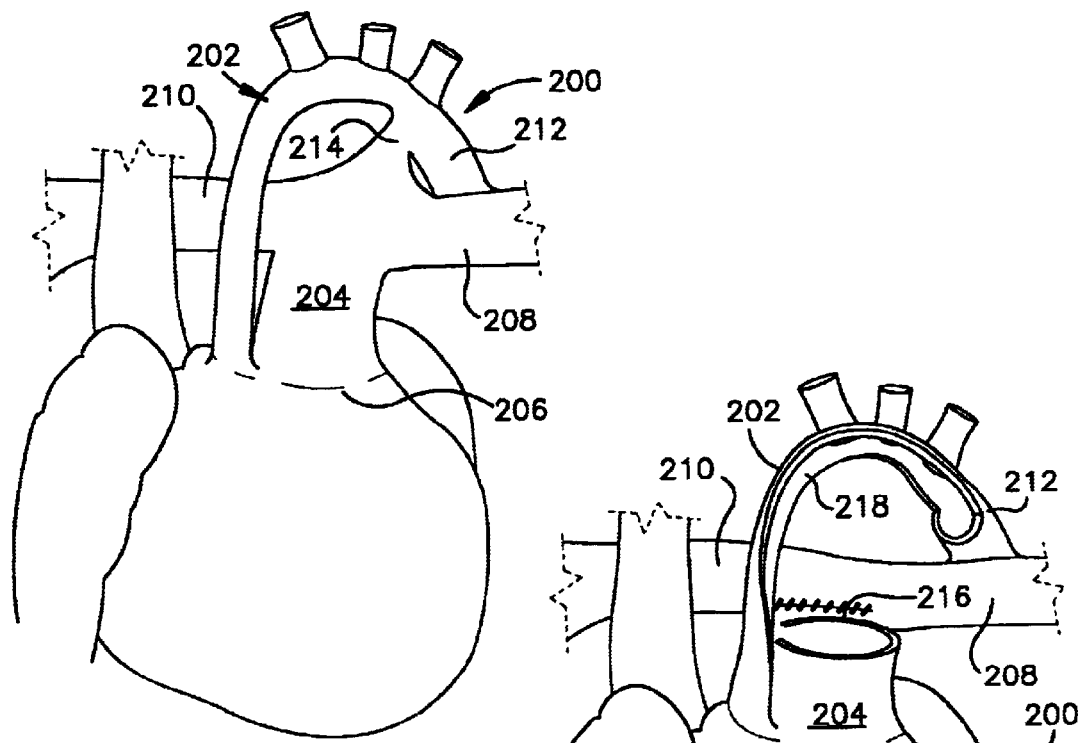
FIG. 13 is an example of heart having a congenital defect.
Figure 14:
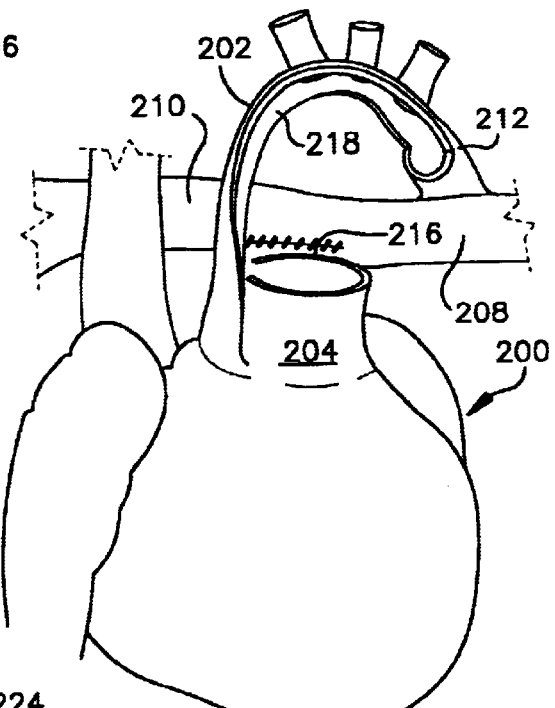
FIG. 14 is the heart of FIG. 13 after part of associated vessels have been removed.
Figure 15:
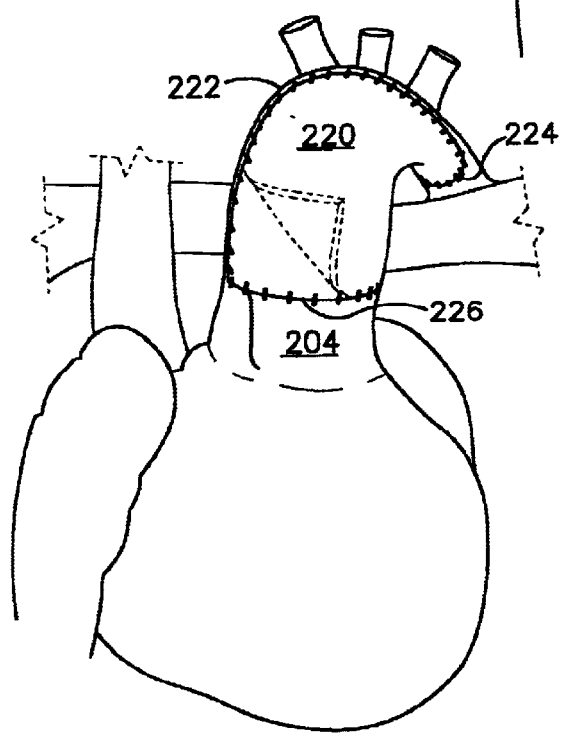
FIG. 15 is an example of a heart in which a curved sheath of tissue has been applied in accordance with the present invention.

By way of illustration, FIGS. 13–15 show part of a procedure (e.g., the Norwood procedure) that utilizes a curved sheath of tissue to repair a defective aorta in accordance with an aspect of the present invention.

FIG. 13 illustrates a heart 200 having a congenital cardiac malformation, such as may occur in an infant suffering from hypoplastic left heart syndrome. As is apparent from the figure, the heart 200 includes a diminutive ascending aorta 202, such as due to severe aortic valve hypoplasia or aortic valve atresia. Thus, one aspect of the procedure is to enlarge the diameter of the aortic arch. Also, as shown in FIG. 13, the main pulmonary trunk 204 extends from the outflow of the left ventricle 206, with left and right pulmonary arteries 208 and 210 branching from the main trunk. The descending aorta 212 also is coupled to the pulmonary artery via a ductus vessel 214.

As shown in FIG. 14, the main trunk of the pulmonary artery 204 has been transected adjacent to the take off at the right pulmonary artery 210. The main pulmonary artery stump is closed, such as by suturing a patch 216 (e.g., a NO-REACT® pericardial patch or a homograft) thereto. The aorta 212 also has been separated from the pulmonary artery by removing the dutus 214.

The aorta 202, 212 also is illustrated in an open condition, such as after having been opened by an axial incision 218. The incision 218 extends from the descending aorta 212 to the ascending aorta 202 near a level proximal the exposed rim of the main pulmonary artery trunk 204.

A curved sheath 220 of biocompatible biological tissue material is anastomosed to the open aorta to enlarge the aorta in accordance with an aspect of the present invention. For example, the sheath 220 has a generally C-shaped cross section and extends arcuately along its length (see, e.g., FIG. 12). The sheath 220 includes side edges 222 that extend arcuately between ends 224 and 226. The end 224 is sewn to the descending aorta 212. The side edges 222 of the curved sheath 220 are then sutured to the exposed edges of the aortic arch defined by the incision 218.

An aperture can be formed through the patch near the end 224 thereof for an aorto-pulmonary shunt, which may be operatively coupled between the aperture and the pulmonary artery. The shunt, for example, could be a short cylinder of a biological tissue material, such as a length of a fixed tubular length of biocompatible material (see, e.g., FIG. 11). Alternatively, the shunt could be formed of a PTFE material or other suitable biocompatible material.

The end 226 of the sheath 220 and part of the ascending aorta, which define an augmented aorta, are then anastomosed to the main pulmonary artery 204. This provides an outflow path from the right ventricle 206 to the augmented aorta. Advantageously, the native portion of the augmented aorta can continue to grow with the patient.

It is to be appreciated that a curved sheath 128, 220 of biological tissue material can be useful in the repair or reconstruction of other types of defects and diseases. In particular, the curved sheath can be utilized in non-cardiac procedures (e.g., neurosurgery, bladder repair, etc.). In addition, while a single arcuate curve is illustrated as extending between the ends of the sheath, it is to be appreciated that any number of curves can be implemented in a sheath in accordance with an aspect of the present invention. The particular dimensions and configuration of a sheath being produced will vary according to its intended application.

What has been described above includes examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims. Furthermore, to the extent that the term "includes" and variants thereof or the term "having" and variants thereof are used in either the detailed description or the claims, each such term is intended to be inclusive in a manner similar to the term "comprising."

What is claimed is:

1. A method for making a sheath having a curved contour, comprising:

providing a sheet of a biological tissue material, the sheet having ends spaced apart from each other by elongated side edges;

forming a generally tubular apparatus from the sheet of the biological tissue material, the forming comprising securing the side edges of the sheet of biological material relative to each other;

urging an elongated member having a curved exterior portion into the tubular apparatus, such that the relative spacing between the side edges of the sheet of biological material remains substantially unchanged;

placing the tubular apparatus and elongated member in a fixation solution so that at least part of the tubular apparatus is fixed to a configuration defined by the exterior portion of the elongated member engaged thereby;

separating the tubular apparatus from the elongated member to provide an elongated sheath of substantially biocompatible material having a curved contour corresponding to the curved exterior portion of the elongated member; and removing a strip of tissue adjacent and coextensive at least one of the side edges of the sheet to form an elongated sheath having a curved contour that extends arcuately between opposite ends thereof and having a generally C-shaped cross section.

2. The method of claim 1, the elongated member having an outer diameter that approximates the diameter of the tubular apparatus.

3. The method of claim 1, the securing of the side edges further comprising suturing the side edges relative to each other to define a suture line that extends between the ends of the tubular apparatus.

4. The method of claim 1, wherein the biological tissue material comprises animal pericardium.

5. An elongated sheath produced according to claim 1, the elongated sheath having a curved contour extending arcuately between opposite ends thereof and having a generally C-shaped cross section.

6. A method for making a sheath having a curved contour, comprising:

providing a sheet of a biological tissue material, the sheet having ends spaced apart from each other by elongated side edges;

forming a generally tubular apparatus from the sheet of the biological tissue material, the forming further comprising securing the side edges of the sheet of biological material relative to each other by suturing to define a suture line that extends between the ends of the tubular apparatus;

urging an elongated member having a curved exterior portion into the tubular apparatus such that the relative spacing between the side edges of the sheet of biological material remains substantially unchanged;

placing the tubular apparatus and elongated member in a fixation solution so that at least part of the tubular apparatus is fixed to a configuration defined by the exterior portion of the elongated member engaged thereby;

separating the tubular apparatus from the elongated member to provide an elongated sheath of substantially biocompatible material having a curved contour corresponding to the curved exterior portion of the elongated member; and removing the suture line to define an elongated sheath having a curved contour that extends arcuately between opposite ends thereof and having a generally C-shaped cross section.

7. An elongated sheath produced according to claim 6.

8. A method of making an implantable sheath having a curved contour, comprising:

providing a sheet of tissue, the sheet having ends spaced apart from each other by elongated side edges;

placing the sheet into engagement with a surface of an elongated member, the surface being curved along at least a portion of a long axis that extends between ends of the elongated member;

applying retaining elements to hold the sheet relative to the elongated member such that at least a substantial portion of the sheet engages the at least part of the curved surface of the elongated member during fixation;

fixing the sheet in a fixation solution while the sheet engages at least part of the curved surface of the elongated member so that at least part of the sheet assumes a contour defined by the at least part of the curved surface of the elongated member engaged by the sheet; and separating the sheet relative from the elongated member to provide an elongated sheath of substantially biocompatible material having a curved contour corresponding to the at least part of the curved surface of the elongated member; and removing the retaining elements after fixation to provide a curved sheath having a generally C-shaped cross-section.

9. The method of claim 8, the elongated member having a generally cylindrical sidewall portion that extends arcuately along its length between opposite ends thereof.

10. The method of claim 9, the sidewall portion of the elongated member having a radius of curvature extending between the opposite ends thereof that is greater than about forty-five degrees.

11. The method of claim 8, the retaining elements including sutures that connect the opposed side edges of the sheet.

12. The method of claim 8, the elongated member extending arcuately between spaced apart ends of the elongated member according to a radius of curvature, such that after fixation the sheath extends arcuately between the ends of the sheet according to the radius of curvature.

13. The method of claim 8, wherein the biological tissue material comprises animal pericardium.

14. An elongated sheath produced according to claim 8.

15. A method of making an implantable sheath having a curved contour, comprising:

providing a sheet of tissue, the sheet having ends spaced apart from each other by elongated side edges;

placing the sheet into engagement with a surface of an elongated member, the surface being curved along at least a portion of a long axis that extends between ends of the elongated member, the elongated member extending arcuately between spaced apart ends of the elongated member according to a radius of curvature;

applying retaining elements to hold the sheet relative to the elongated member such that at least a substantial portion of the sheet engages the at least part of the curved surface of the elongated member during fixation;

fixing the sheet in a fixation solution while the sheet engages at least part of the curved surface of the elongated member so that at least part of the sheet assumes a contour defined by the at least part of the curved surface of the elongated member engaged by the sheet; and separating the sheet relative from the elongated member to provide an elongated sheath of substantially biocompatible material having a curved contour corresponding to the at least part of the curved surface of the elongated member; and removing the retaining elements together with a strip of tissue from the sheet located adjacent and coextensive to at least one of the side edges of the sheet to form an elongated sheath having a curved contour that extends arcuately between opposite ends thereof and having generally C-shaped cross section.

* * * * *